United States Patent [19]

Krauth

[11] Patent Number: 4,954,435

[45] Date of Patent: Sep. 4, 1990

[54] INDIRECT COLORIMETRIC DETECTION OF AN ANALYTE IN A SAMPLE USING RATIO OF LIGHT SIGNALS

[75] Inventor: Gary H. Krauth, Jordan, Utah

[73] Assignee: Becton, Dickinson and Company, Franklin Lakes, N.J.

[21] Appl. No.: 2,334

[22] Filed: Jan. 12, 1987

[51] Int. Cl.$^5$ .................. G01N 33/53; G01N 33/543; C12Q 1/28; G01J 3/42
[52] U.S. Cl. ........................................ 435/7; 356/320; 356/341; 356/407; 435/25; 435/28; 436/518; 436/527; 436/531; 436/534; 436/537; 436/544; 436/805; 436/811; 436/817; 436/818
[58] Field of Search ............... 435/25, 28, 7; 436/517, 436/537, 805, 909, 518, 527, 581, 534, 544, 811, 818, 817; 356/320, 407, 341, 441

[56] References Cited

U.S. PATENT DOCUMENTS

| 3,527,538 | 8/1965 | Allen et al. | 356/368 |
|---|---|---|---|
| 3,781,112 | 12/1973 | Groner et al. | 356/39 |
| 3,813,168 | 5/1974 | Honkawa | 356/320 |
| 4,495,273 | 1/1985 | Shaffar | 436/172 |
| 4,503,143 | 5/1985 | Gerber et al. | 435/7 |
| 4,680,274 | 7/1987 | Sakai et al. | 436/512 |
| 4,680,275 | 7/1987 | Wagner et al. | 436/805 |
| 4,714,672 | 12/1987 | Rokugawa et al. | 436/805 |
| 4,743,561 | 5/1988 | Shaffar | 436/805 |

OTHER PUBLICATIONS

"A Nephelometry System for the Abbot TDx ® Analyzer" R. F. DeGrella et al, Clinical Chemistry 31(9); 1474-77; 1985.

"3,3',5,5'-Tetramethylbenzidine as an Ames Test Negative Chromogen for Horse-Radish Peroxidase in Enzyme-Immunoassay", E. S. Bos et al, J. of Immunoassay, 2(3 & 4); 187-204, 1981.

*Primary Examiner*—Esther L. Kepplinger
*Assistant Examiner*—Florina B. Hoffer
*Attorney, Agent, or Firm*—Aaron Passman

[57] ABSTRACT

The method of the present invention employs an enzyme immunoassay for measuring the concentration of an analyte in a sample by indirect colorimetric detection. An incident light beam at a plurality of wavelengths is directed into a liquid solution containing an analyte of interest. The solution is capable of attenuating the amount of light at a first wavelength received from this solution as a function of the increasing concentration of the analyte present. A light signal from the solution at the first wavelength is detected, and light at a second wavelength, at which substantially no attenuation of light signal occurs as the concentration of the analyte increases, is also detected. The ratio of the two respective wavelengths is formed and that ratio is compared with ratios of known amounts of the analyte to determine the amount of the analyte in the sample.

4 Claims, 7 Drawing Sheets

INDIRECT COLORIMETRIC DETECTION OF AN ANALYTE IN A SAMPLE USING RATIO OF LIGHT SIGNALS

BACKGROUND OF THE INVENTION

1. Field of the Invention

The present invention relates to a method for the detection of an analyte in a sample, and more particularly concerns a method employing an enzyme immunoassay for measuring the concentration of an analyte in a sample by indirect colorimetric detection.

2. Background Description

Assays for the colorimetric detection of analytes are common and well-known. In particular, enzyme immunoassays (EIA) and enzyme-linked immunosorbent assays (ELISA) are employed for the colorimetric detection of an antigen (analyte) present in a test sample. In these enzyme immunoassay methods, antibodies specific to the test antigen or analyte are bound to a solid phase which is usually a clear or transparent plastic tube. In many, but not all, of these enzyme immunoassays, a sandwich formation occurs between the solid phase antibody, the antigen and the enzyme-labeled antibody such that the amount of enzyme-labeled antibody bound to the solid phase is directly proportional to the antigen concentration in the sample. Excess, unreacted reagents are normally washed from the tube, and substrate is added to effect the enzyme reaction.

In addition to sandwich formation, which typically occurs with protein antigens, it is possible to perform competitive assays. A limiting amount of antibody is put on the solid phase, and both sample and an enzyme-labeled hapten are simultaneously incubated. When no analyte is present in the sample, the enzyme-labeled hapten binds maximally to the solid phase. As the amount of analyte in the sample increases, it competes with the enzyme-labeled hapten for binding to the solid phase such that the amount of enzyme-labeled hapten binding is inversely proportional to the analyte concentration. Competitive assays may be performed for both haptens and protein analytes, but only protein analytes are amenable to a sandwich-type assay.

In colorimetric detection techniques, the substrate may include a chromogenic substance which is responsive to the enzyme so that the chromogenic substance is activated. As a result, sufficient color is produced in the liquid solution within the tube which may be detected. Assays of this nature are frequently completed by measuring the color production within the tube by use of a spectrophotometer. In the event that fluorochromes are used as the substances to be detected, fluorescence microscopes as well as fluorometers may be used to perform the assay methods. An enzyme immunoassay using a tetramethylbenzidine (TMB) as the chromogen in the colorimetric detection of an antigen is described in U.S. Pat. No. 4,503,143.

In using a spectrophotometer for the colorimetric detection of an analyte in a sample, there are a number of factors which may affect the detection of light associated with the chromogenic reaction. For instance, the light source for providing an incident beam of light into the tube containing the sample to be tested is frequently a lamp, for instance, a tungsten lamp, such as that described in U.S. Pat. No. 4,516,856. It is not uncommon to have variations in lamp output which may affect the light detected in a spectrophotometer or light collected in a photomultiplier for detecting fluorescence emissions. Positioning of the tube containing the sample to be tested may be different from test to test, also having an affect on the test results. Other factors such as light path length and optical quality of the tube may produce differences from test to test which may affect the assay results. It is believed that a technique which corrects or obviates the aforementioned variables in colorimetric detection methods would be most desirable in improving the accuracy, reproducibility and reliability of these test procedures.

Improvements in fluorometric assays have been described in U.S. Pat No. 4,495,293. However, the object of the just-mentioned patent is to provide improvements in the fluorescent intensity of the emitted light which is related to the concentration of the ligand. Another technique for the assays of macromolecules by immunonephelometry is described by DeGrella et al. in "A Nephelometry System for the Abbott TDx[198]," Clin. Chem. 31/9, 1474–1477 (1985). A nephelometric method for monitoring chromogenic reactions is described in this publication, which method relies on scattered energy attenuation to measure serum proteins. There are no teachings or suggestions, however, in the DeGrella et al. article which would be useful in correcting for the variables, as set forth above, which affect the assay measurements.

Accordingly, improvements are still being sought in assays relying on the colorimetric detection of the analytes of interest. The present invention is directed to such an improvement.

SUMMARY OF THE INVENTION

The method of the present invention for the detection of an analyte in a sample comprises directing an incident light beam at a plurality of wavelengths into a liquid suspension or solution containing an analyte of interest. This liquid is capable of attenuating the amount of light at a first wavelength proportional to the increasing concentration of the analyte present in the sample. The method further comprises detecting light signals from the liquid related to the first wavelength, and at a second wavelength at which substantially no attenuation of light occurs as the concentration of the analyte increases. A ratio of the two respective wavelengths is formed. This ratio is then compared with ratios of known amounts of the analyte to determine the amount of the analyte in the sample.

One embodiment of the invention is a method employing an enzyme immunoassay for measuring the concentration of an analyte in a sample by indirect colorimetric detection, in which light scatter attenuation is utilized. This method comprises combining an enzyme-labeled antibody conjugate, a sample to be tested for an analyte, and an antibody bound to a solid support so that the analyte binds to the bound antibody and to the conjugate to form an immunologic complex in solid phase. Further, this method includes admixing a liquid solution, containing a chromogenic substance responsive to the enzyme, with the immunologic complex to cause a reaction which activates the chromogenic substance. Particles, capable of causing light scatter at or near the absorbance maximum of the chromogenic substance, are added to the admixture to form a stable suspension. The method further includes directing incident light at a plurality of wavelengths into the suspension. A first wavelength of the incident light is substantially the same as a wavelength maximally absorbed by the chromogenic substance. The chromogenic substance is capable of absorbing increasing amounts of light at the maximum wavelength as the concentration of the chromogenic substance increases. A second wavelength of the incident light beam is spectrally removed from the wavelength maximally absorbed by the chromogenic substance. Light scattered by the suspension at the first and second wavelengths is detected, and a ratio of the two respective wavelengths is formed. The next step of the method is comparing the magnitude of the ratio with the magnitude of the ratio associated with light scatter detection when the previous steps are performed with samples containing known concentrations of the analyte, so that the concentration of the analyte in the sample may be measured.

Another embodiment of the invention is a method employing an enzyme immunoassay for measuring the concentration of an analyte in a sample by indirect colorimetric detection, in which fluorescence is utilized. In this method, an enzyme-labeled antibody conjugate is combined with a sample to be tested for an analyte and an antibody bound to a solid support so that the analyte binds to the bound antibody and to the conjugate to form an immunologic complex in solid phase. This method includes admixing a liquid solution, containing a chromogenic substance responsive to the enzyme, with the immunologic complex to cause a reaction which activates the chromogenic substance. To this admixture is added a first fluorophore for causing fluorescence at or near the absorbance maxima of the attenuating chromogenic substance as a function of the increasing concentration of the analyte present in the sample. Added to this admixture is a second fluorophore which has substantially no attenuation by the Chromogenic substance of its fluorescence as the concentration of the analyte increases. Incident light is directed in a plurality of wavelengths through the tube into the solution. These wavelengths of light include a wavelength at or near the absorbance maxima of the activated chromogenic substance, and includes wavelengths for causing excitation of the first and second fluorophores. Fluorescence emitted by the fluorophores in the solution is detected. This method includes forming a ratio of the two fluorescence wavelengths. The magnitude of the formed ratios is compared with the magnitude of a ratio associated with fluorescence detection when the previous steps are performed with samples containing known concentrations of the analyte, so that the concentration of the analyte in the sample may be measured.

In accordance with the principles of the present invention, colorimetric detection is achieved using indirect techniques, such as the collection of light scatter or fluorescence signals. Examining the ratio of light provides a system which indirectly measures the amount of color generated in an assay, such as an enzyme immunoassay. Further, using a ratio of light signals, one signal of the ratio being the reporter signal and the other being a reference signal, provides a correction mechanism for obviating such variables as fluctuation in the lamp output, variations in tube position, diameter or optical quality. Moreover, use of the above-described ratio also overcomes differences in the concentration of the particulate matter which is added to the admixture for light detection purposes, when light scatter attenuation is utilized. Another advantage of adding particulate matter to the aforementioned admixture is that the particles may be selected to form a stable suspension whose light scattering or other light signal capability is temperature insensitive.

Therefore, the present invention permits the indirect colorimetric determination of the concentration of the analyte by measuring the degree of light signal, preferably light scatter or fluorescence. In addition to negating the problematical variables as mentioned above, the preferred method of the present invention allows for a sensitive detection of the analyte of interest since low concentrations of preferred chromogenic substances, used in the present method, affect the degree of light scatter or fluorescence. Other advantages and features of the present invention will become more apparent from reading the detailed description below.

DETAILED DESCRIPTION

Figure 1:
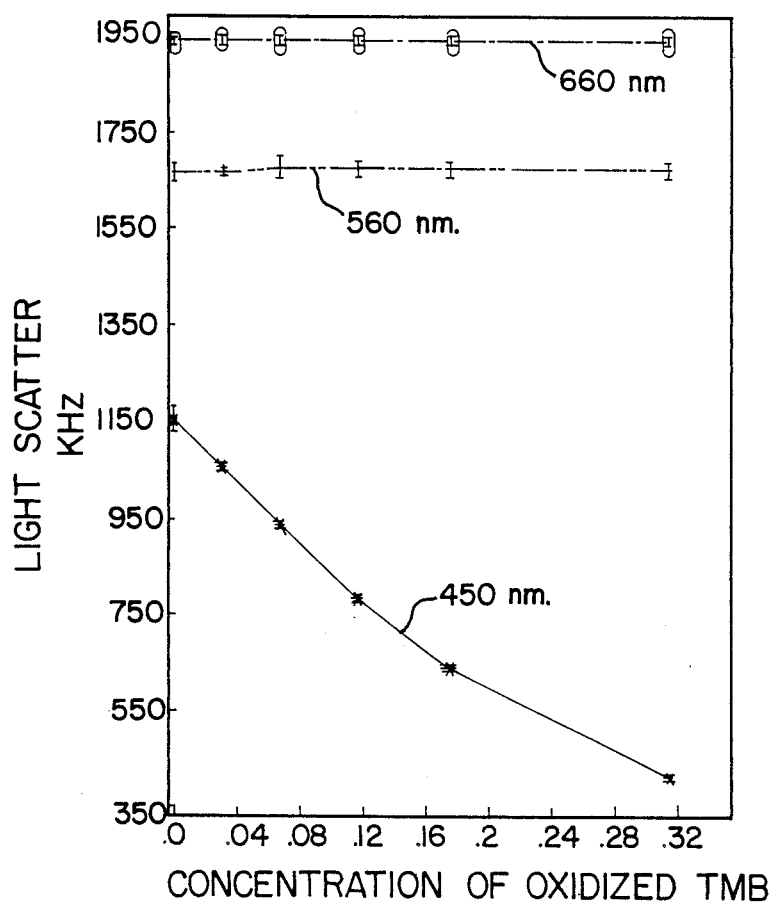
FIG. 1 is a graphic representation of the measurement of light scattering, at three wavelengths, as a function of the concentration of oxidized tetramethylbenzidine (TMB)

While this invention is satisfied by embodiments in many different forms, there is shown in the drawings and will herein be described in detail preferred embodiments of the invention, with the understanding that the present disclosure is to be considered as exemplary of the principles of the invention and is not intended to limit the invention to the embodiments illustrated. The scope of the invention will be measured by the appended claims and their equivalents.

The nature of the present invention is to provide an improvement of preferably those enzyme immunoassays which use chromogenic substances for the colorimetric detection of analytes, including antigens and antibodies. The improvements provided by the present invention, however, as set forth above, are related to a technique which indirectly determines the color generated by the assay in order to determine the concentration of the analyte in the sample.

Rather than rely on the direct measuring of color production, by the use of a spectrophotometer or the like, the present technique uses fluorescence or light scatter measurements in the determination of the amount of analyte present in the sample, it being understood that other light signals, such as absorbance, may also be detected for the indirect colorimetric techniques of the present invention. It has been ascertained that the degree of light scattered or the fluorescence emitted by the liquid sample being assayed may be found as a function of the concentration of the chromogenic substance used in the enzyme immunoassay. Attenuation occurs when the wavelength of the incident light is the same as, or substantially the same as or near, the wavelength maximally absorbed by the chromogenic substance. Therefore, as the concentration of the chromogenic substance increases, the amount of incident light absorption increases while the degree of light scatter or fluorescence decreases.

One exemplary chromogenic substance useful in the present invention is a tetramethylbenzidine (TMB) in hydrogen peroxide. When TMB is employed as the substrate in an enzyme immunoassay, in which the enzyme is preferably peroxidase, the enzyme converts the TMB to an oxidized form in the presence of a co-substrate, hydrogen peroxide. At neutral pH, oxidized TMB exhibits two principal absorption maxima in the visible portion of the spectrum. One absorption maxima is centered approximately at 450nm, and the other maxima substantially at 655nm. Upon acidification with a strong, non-oxidizing acid, the absorption at 655nm disappears, while the band at 450 nm remains, but with a higher extinction coefficient (see, E.S. Bos et al., 3,3′,5,5′-tetramethylbenzidine as an Ames Test Negative Chromogen for Horse-Radish Peroxidase in Enzyme Immunoassay, *Journal of Immunoassay* 2, 187 (1981)).

In accordance with one aspect of the present invention, instead of measuring the color generated by a chromogenic substance, such as TMB, a light signal, such as light scattering, is detected. The addition of a light scattering source, such as fumed silica particles or polystyrene microbeads, to the oxidized TMB results in attenuation of the light scattering, when measured at 450nm, as a function of the amount of oxidized TMB present and, hence, indirect measurement of the analyte concentration in the assayed sample. The attenuation of light scatter ,measured at 450nm as a function of concentration of oxidized TMB is illustrated in FIG. 1. The attenuation of light scatter at 450nm is related to the absorption characteristics of the chromogenic substance. Specifically, as the concentration of oxidized TMB increases, the amount of light absorption increases and the amount of light scatter decreases when the wavelength of the incident light is the same as the wavelength of maximum absorption of the oxidized TMB, in this instance, at 450nm. On the other hand, it can be seen in FIG. 1 that the light scatter measured at two other wavelengths, spectrally removed from the wavelength of maximum absorption of the TMB, is not attenuated over the concentration range set forth. Indeed, as the light scatter detection at 560nm and 660nm remains substantially constant over the concentration range, light scatter at these two frequencies may be used as internal referencing wavelengths, since their magnitudes are independent of the concentration of the light absorbing substance. Accordingly, a ratio may be formed with the light scatter measured at the wavelength of maximal absorption of the chromogenic substance and at another wavelength spectrally removed from the wavelength of maximal absorption and which is independent of the concentration of the chromogenic substance. These light scatter ratios, determined as a function of concentration of oxidized TMB, are illustrated in FIG. 2.

Figure 2:
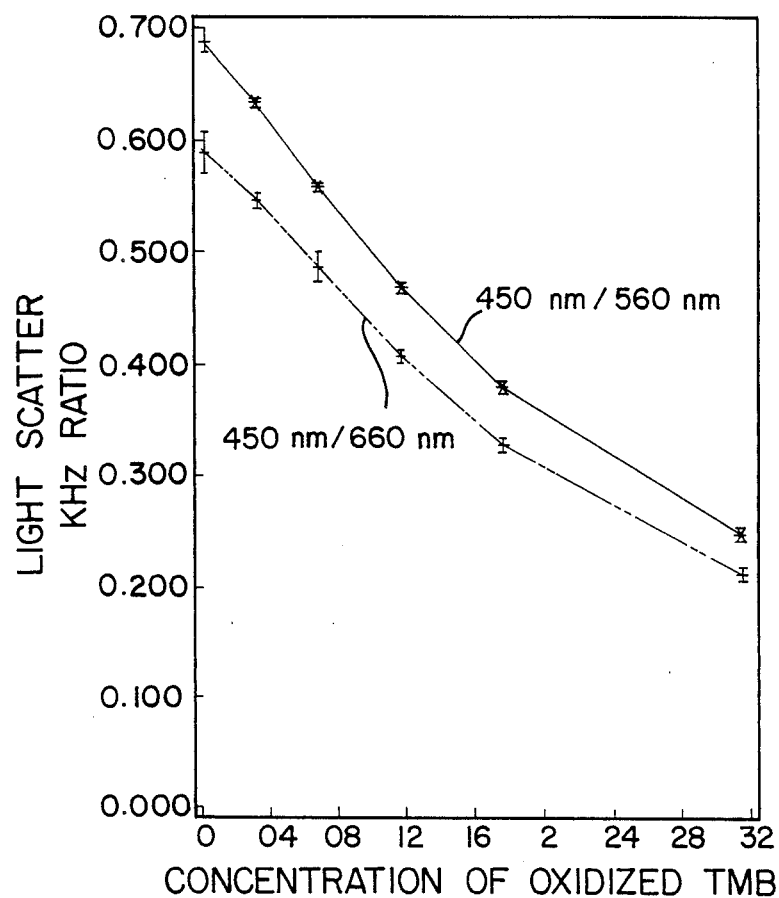
FIG. 2 is a graphic representation of two ratios of different wavelengths of light scatter measured as a function of the concentration of oxidized tetramethylbenzidine (TMB), in accordance with the principles of the present invention.

It can be seen in FIG. 2 that two ratios have been measured, one at 450nm/560nm and the other at 450nm/660nm. Both of these ratios track the attenuation curve of the oxidized TMB illustrated in FIG. 1. FIG. 2, however, demonstrates that the precision of the 450nm/560nm ratio is somewhat better than the 450nm/660nm ratio. It is understood that light scatter may be measured at frequencies other than 560nm and 660nm in order to establish ratios in which one of the wavelengths is independent of the concentration of the chromogenic substance. By establishing the ratio of light scattering at such frequencies as illustrated in FIG. 2. an internal correction is provided for the detection system, which negates differences in length of the light path, optical quality of the sample tube, tube positioning, variations in lamp output and even differences in the concentration of the light scatter source added to the sample.

Another indirect colorimetric technique for the detection of an analyte in a sample involves the use of two fluorophores. Instead of measuring the light scatter characteristics of the liquid solution containing the chromogenic substance, such as TMB, fluorescence is measured. One of the fluorophores serves as a reporter signal, while the other fluorophore serves as a reference signal.

The fluorophores used in this approach are chosen or selected so that their respective wavelengths of excitation and emission are substantially spectrally separated from each other. Keeping this feature in mind, the fluorophore which is to serve as the reporter is selected so that its wavelengths of excitation and emission are at or substantially near the absorbance maxima of the chromogenic substance. For example, as pointed out above, the absorbance maxima of oxidized TMB is at 450 nm. It has been determined that the degree of fluorescence is attenuated by absorbance as a function of the concentration of the chromogenic substance, such as oxidize TMB, if the wavelength of either the excitation or emission of the fluorophore is at or substantially near the wavelength as that maximally absorbed by the oxidized TMB. As the concentration of the chromogenic substance increases, the amount of incident light absorption increases, while the degree of fluorescence decreases.

On the other hand, the second fluorophore is selected so that it has a wavelength of excitation or emission spectrally removed from the wavelength representing the absorption maxima of the chromogenic substance. Measuremen of the fluorescence emitted by the second or reference fluorophore in a spectral region that does not overlap the absorption spectrum of the chromogenic substance is independent of the concentration of the absorbing species. By examining the ratio of fluorescence of the reporter fluorophore, at or substantially near the wavelength of maximum absorbance of the chromogenic substance, to that of the reference fluorophore in a region spectrally removed from the asorption spectrum of the chromogenic substance provides a measurement technique that indirectly measures the amount of color generated in an enzyme immunoassay.

Reliance on the ratio of fluorescence signals, one fluorophore being the reporter and the other fluorophore being the reference, provides the same advantageous features as the previously described light scatter ratio for the indirect colorimetric detection of the analyte in a sample.

When the fluorescence ratio technique is employed, the preferred chromogenic substance is TMB which, when oxidized, has an absorption maxima substantially at 450 nm. A number of fluorophores are available which have a wavelength of excitation or emission at or nearly the same as the absorption maxima of oxidized TMB. For example, Coumarin 343, 9-aminoacridine hydrochloride and 8-methoxypyrene1,3,6-trisulfonic acid (MPT) are good candidates as the reporter fluorophore, with MPT being preferred. MPT is excited at about 395 nm, and has a peak emission at about 430 nm. These wavelengths are relatively close to the absorption maxima of oxidized TMB at 450 nm.

Different fluorophores may also be selected as the reference fluorophore, including oxazine 170 perchlorate and, preferably, sulforhodamine 101 (SR 101). SR 101 is excited at 589nm, and provides a peak emission at about 605 nm. Thus, it can be seen that the excitation and emission wavelengths of SR 101 are substantially spectrally separated or removed from the wavelength of absorption maxima of the oxidized TMB, as well as the wavelengths of excitation and emission of the reporter fluorophore, such as MPT. This spectral separation allows for the detection of a fluorescence signal which is independent of the concentration of the absorbing species.

Further, with respect to the reference fluorophore, it should be chosen so that there is no, or substantially no, attenuation by absorption of the signal relative to the different concentrations of the chromogenic substance, such as TMB. In this regard, the reference fluorophore serves as an internal referencing system correcting for a number of factors, including tube position, diameter or optical quality. Therefore, in selecting the respective reporter and reference fluorophores, the reporter fluorophore should have its degree of fluorescence attenuated by absorbance as a function of the concentration of the chromogenic substance at or near its absorption maxima, while the degree of fluorescence of the reference fluorophore should remain relatively constant as a function of the concentration of the chromogenic substance. It should be noted that some fluorophores, such as SR 101, may serve as the reference fluorophore as long as the degree of fluorescence remains fairly constant, as a function of the chromogenic substance, for short periods of time after the addition of the stopping reagent, such as less than two minutes.

Enzyme immunoassays for a number of analytes are the assays of choice for the indirect colorimetric detection methods of the present invention. For example, analytes such as human chorionic gonadotropin (hCG) are assayed in testing for the pregnancy of women; luteinizing hormones (hLH) are assayed in the testing of fertility of women; thyroid stimulating hormone; thyroxine; and assays for the testing of certain bacteria and microorganisms are performed using enzyme immunoassays and colorimetric detection techniques. The present invention, however, is not limited to the detection of the aforementioned analytes, since such analytes are merely exemplary of the many different kinds of analytes which may be measured employing the indirect light detection techniques of the present invention.

In addition to the use of TMB in hydrogen peroxide as the chromogenic substance, it is understood that other chromogenic substances may be used in the present invention. The techniques of the present invention, as described above, may be applied to various enzyme or substrate systems by measuring the light scatter or fluorescence at or near the wavelength of maximum absorbance of the chromogenic substance and referencing at a wavelength removed from its absorption spectrum and which is independent of the concentration of the analyte of interest. Thus, besides TMB, other representative chromogenic substances include the benzidines, o-phenylenediamine, o-tolidine and ABTS. Use of TMB in hydrogen peroxide, such as that described in U.S. Pat. No. 4,503,143, is the preferred chromogenic substance for use in the present invention.

In the EIA procedures contemplated hereby, the enzyme is employed to label the analyte, such as an antibody or antigen, and to catalyze the chromogenic reaction. Desirable enzymes are the oxidoreductases, particularly the heme enzymes including catalase and peroxidase. These enzymes have distinctive absorption spectra due to their heme prosthetic groups and show transient changes in their spectra on mixing with hydrogen peroxide, their substrate. One particularly desired enzyme which catalyzes TMB is horseradish peroxidase.

Regarding the particles which are added to the assay sample as a light scattering source a number of alternatives are available. Microparticles, having an average diameter ranging between 0.010 and 0.014 microns, are preferably included in the liquid solution through which light is directed so that, when light strikes these particles, a scattering effect results. Microbeads, such as those made of polystyrene or other materials having a density approximately the same as the density of water, are suitable as a source for providing the light scattering effect. It is preferred that such microbeads have substantially no secondary emission properties which may distort the readings. Most preferably, however, it has been found that microparticles, in the above-mentioned size range, formed of fumed silica perform most satisfactorily in the present invention. It has been found that a dilution of fumed silica in citric acid produces a light scatter response which is linear with the concentration of fumed silica up to 0.3% (w/v). Indeed, the amount of fumed silica added to different tubes may vary without affecting the light scatter readings, because the measurement of light scattering as a ratio compensates for such differences.

Well-known enzyme immunoassay techniques may be employed hereunder. For instance, a test tube or the like, typically made from clear or transparent plastic, includes an antibody, for the antigen or analyte of interest, bound to the interior surfaces thereof. In one or more steps, an enzyme-labeled antibody conjugate and a liquid sample to be tested for the analyte are combined in the tube so that the analyte binds to the bound antibody and to the conjugate to form an immunologic complex in solid phase. This immunologic complex is representative of a sandwich formation occurring between the solid phase antibody, the analyte and the enzyme-labeled antibody such that the amount of enzyme-labeled antibody bound to the solid phase is directly proportional to analyte concentration in the sample. In usual fashion, unreacted reagents are washed from the tube, and substrate is then added to initiate the enzyme reaction.

In a preferred embodiment hereunder, the enzyme reaction includes the addition of both hydrogen peroxide- and TMB to the tube, whereby the TMB is activated (oxidized) resulting in the generation of color within the tube after a given period of time. The concentration of the oxidized TMB within the tube is directly proportional to the concentration of the analyte in the sample An acid solution is then added to the tube in order to terminate the enzyme reaction. Assays of this type may be reported by measuring the light signal by use of a spectrophotometer or fluorometer. These color-detecting instruments are well-known and typically include a lamp as a light source, a stage or device for holding the test tube, a photomultiplier tube and optics to detect the light. Inasmuch as scatter light may be detected in any direction, the positioning of the light detection devices within the instrument may vary. For example, if a fluorometer is to be used, fluorescence is detected at 90° relative to the incident light beam. In accordance with another aspect of this invention, the optics of the fluorometer may be modified so that light scatter, instead of fluorescence, is detected at 90° relative to the incident light beam. In spectrophotometers, color may be measured in the forward direction relative to the incident light beam; those instruments may be modified to detect scatter, rather than color, in the forward direction. Light scatter may be detected in other directions, as well.

When using a lamp, such as a tungsten lamp, as the light source, a spectrally rich beam of light is typically provided having wavelengths between 350nm and 800 nm. With such spectrally rich light, it may be necessary to filter the light beam on the incident side of the test tube or on the scattered side, or both. By using the appropriate filters, it is possible to obtain the highest possible signal, whether light scatter or fluorescence, at the wavelength of maximal absorption by the chromogenic substance. Selection and positioning of the appropriate filters depends upon the chromogenic substance of choice since the wavelength of attenuation by absorbance and the referencing wavelength may vary from substance to substance. Filter selection and positioning may be readily performed by one having ordinary skill in the field of optics.

The following examples are provided as exemplary of the techniques of the present invention, but it is understood that the invention is not to be construed as limited thereto.

EXAMPLE I

Figure 3:
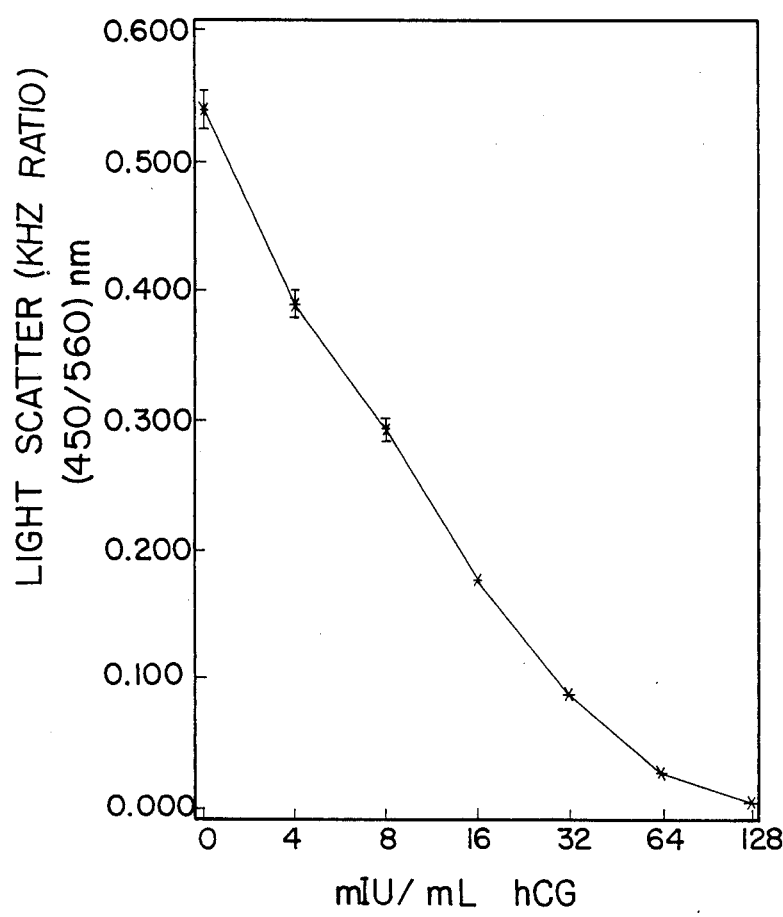
FIG. 3 is a graphic representation of a ratio of light scatter measured as a function of the concentration of human chorionic gonadotropin (hCG), carrying out the principles of the present invention in an enzyme immunoassay.

A light transparent polystyrene tube had its interior surfaces coated with anti-hCG. To this tube was added 100 microliters of 1:50 dilution of anti-hCG peroxidase-labeled conjugate, and 100 microliters of a liquid sample to be tested for, and believed to contain, hCG. The reaction was allowed to proceed for 30 minutes at 37° C., and the incubate was then aspirated. After washing the tube three times each with two milliliters of- 0 05% Tween in water, 200 microliters of substrate, containing both tetramethylbenzidine (TMB) and hydrogen peroxide, were added, and the mixture was allowed to incubate for 30 minutes at room temperature. To the tube was then added one milliliter of 1M citric acid containing 0.3% (w/v) of fumed silica particles having an average diameter of about 0.014 microns. The tube was then placed in an optically-modified fluorometer and light wa directed through the walls of the tube into the suspension. Light scattered at 90° relative to the incident light beam was detected at both 450nm and 560 nm, and the results were expressed as a ratio of the two wavelengths. A standard curve was prepared, by using the same steps as outlined above, with samples containing known concentrations of hCG, and the data related thereto are shown in the curve of FIG. 3. By comparing the ratio of the unknown sample expressed by the instrument with the ratio of the standard curve of FIG. 3, the hCG concentration in the unknown sample was determined.

EXAMPLE II

Figure 4:
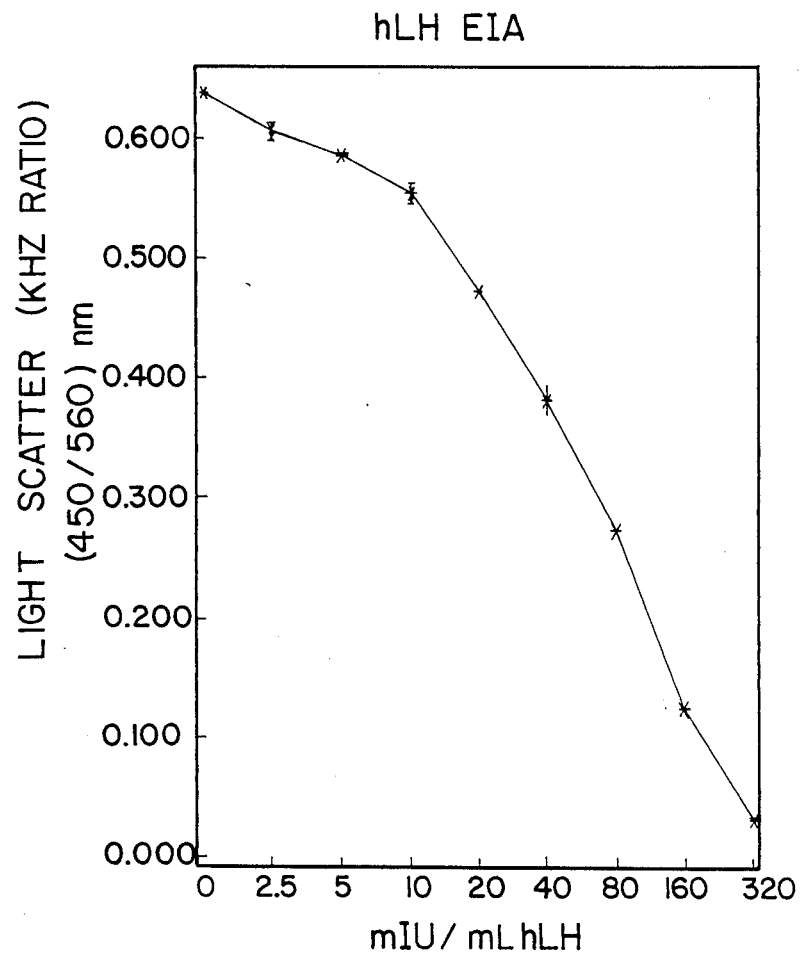
FIG. 4 is a graphic representation of a ratio of light scatter measured as a function of the concentration of human luteinizing hormone (hLH), carrying out the principles of the present invention in an enzyme immunoassay.

A light transparent polystyrene tube had its interior surfaces coated with anti-hLH. To the tube was added 100 microliters of a 1:50 dilution of anti-hLH peroxidase-labeled conjugate, and 100 microliters of a sample t be tested for, and believed to contain, hLH. The reaction was allowed to proceed for one hour at 37° C., and the incubate was then aspirated. The tube was washed three times with two milliliters each of 0.05% Tween in water. To the washed tube were added 200 microliters of substrate, containing both tetramethylbenzidine (TMB) and hydrogen peroxide, and the reaction was allowed to proceed for 30 minutes at room temperature. The reaction was terminated by adding one milliliter of 1M citric acid containing 0.3% (w/v) particles of fumed silica having an average diameter of about 0.014 microns. The tube was positioned in a fluorometer instrument optically modified to read light scatter collected at 90° relative to the incident light beam. Light scatter was detected at both 450nm and 560nm and the results were expressed as a ratio of the light scattering at the two wavelengths. A standard curve was prepared in which the ratios were measured as a function of known concentrations of hLH. This standard curve is illustrated in FIG. 4. In the sample under test, the ratio of light scatter expressed by the instrument was compared to the standard curve of FIG. 4 so that the concentration of hLH in the unknown sample was able to be ascertained.

EXAMPLE III

Figure 5:
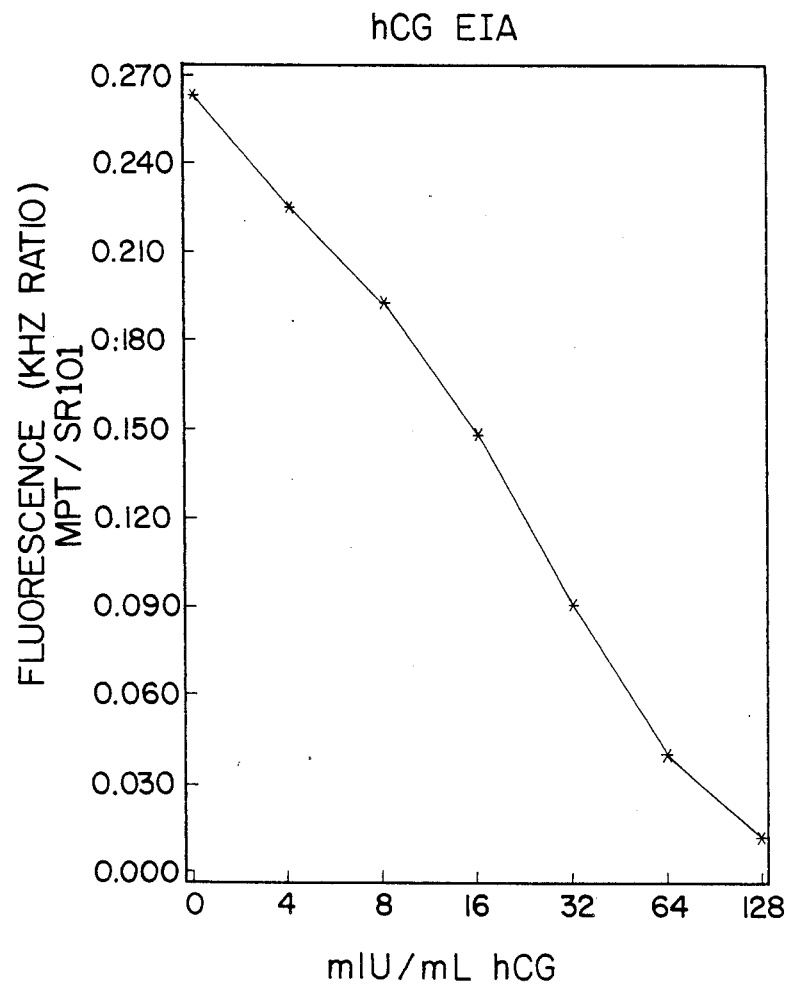
FIG. 5 is a graphic representation of a ratio of fluorescence signals measured as a function of the concentration of human chorionic gonadotropin (hCG), carrying out the principles of the present invention in an enzyme immunoassay.

A light transparent polystyrene tube had its interior surfaces coated with anti-hCG. To this tube was added 100 microliters of 1:200 dilution of anti-hCG peroxidase-labeled conjugate, and 100 microliters of a liquid sample to be tested for, and believed to contain, hCG. The reaction was allowed to proceed for 15 minutes at 37° C., and the incubate was then aspirated. After washing the tube three times each with 2 milliliters of 0.05% Tween in water, 200 microliters of substrate, containing both TMB and hydrogen peroxide were added to each tube. The TMB contained 1.7 micro-M MPT and 8.6 micro-M SR 101. This mixture was allowed to incubate for 15 minutes at 37° C. To the tube was then added 0.8 milliliters of 1 M citric acid. The tube was then placed in a fluorometer which included a 395nm filter on the excitation side and a 430nm filter on the emission side for the MPT fluorophore. The fluorometer included a 589 nm filter on the excitation side and a 605nm filter on the emission side for the SR 101 fluorophore. Light from a lamp was directed through the walls of the tube into the solution. Fluorescence was detected at 430nm and 605nm, and the results were expressed as a ratio of the two wavelengths. A standard curve was prepared, by using the same steps as outlined above, with samples containing known concentrations of hCG, and the data related thereto are shown in the curve of FIG. 5. By comparing the fluorescence ratio of the unknown sample expressed by the instrument with the ratio of the standard curve of FIG. 5, the hCG concentration in the unknown sample was determined.

EXAMPLE IV

Figure 6:
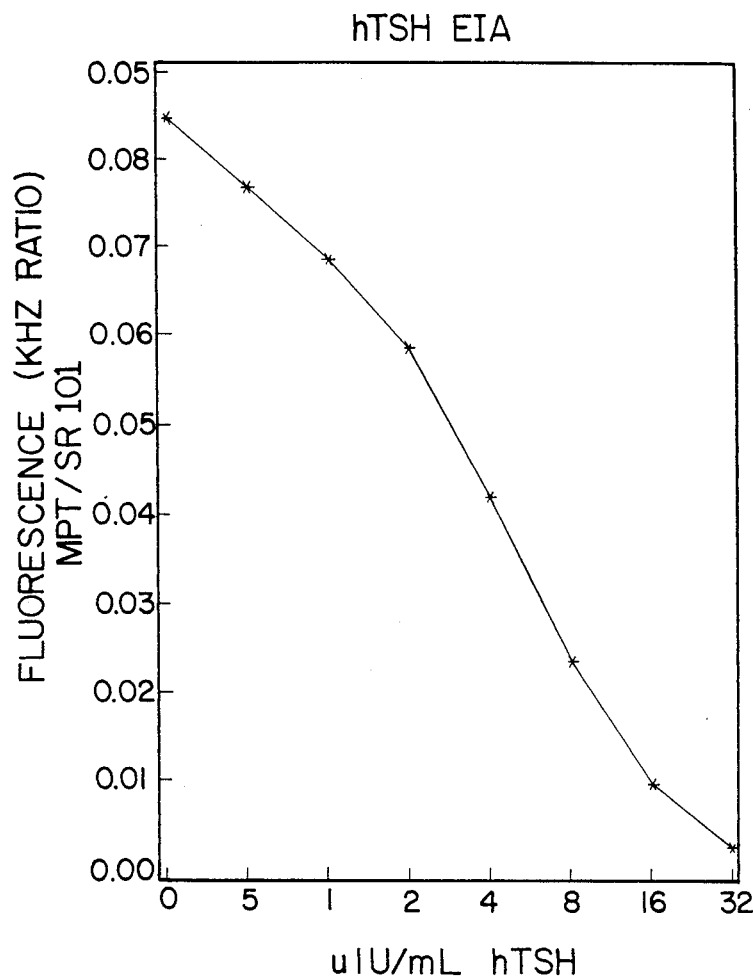
FIG. 6 is a graphic representation of a ratio of fluorescence signals measured as a function of the concentration of human thyroid stimulating hormone (hTSH), carrying out the principles of the present invention in an enzyme immunoassay.

In a procedure similar to the previous examples, a tube was coated with anti-hTSH. To this tube was added 100 microliters of a 1:200 dilution of anti-hTSH peroxidase-labeled conjugate and 200 microliters of a sample to be tested for, and believed to contain, hTSH. The reaction was allowed to proceed at 30 minutes at 37° C. and the incubate was then aspirated. The tube was washed three times with two milliliters each of 0.05% Tween in water. To the washed tube was added 300 microliters of substrate, containing TMB and hydrogen peroxide, and the two fluorophores as above, MPT and SR 101. The reaction was allowed to proceed for seven minutes aat 37° C., and the reaction was stopped by adding 0.8 milliliters of 1 M citric acid. The tube was read in the fluorometer as described in Example III, and the results were expressed as a ratio of MPT/SR 101 to the concentration of hTSH originally in the sample. Typical results are illustrated in FIG. 6.

EXAMPLE V

Figure 7:
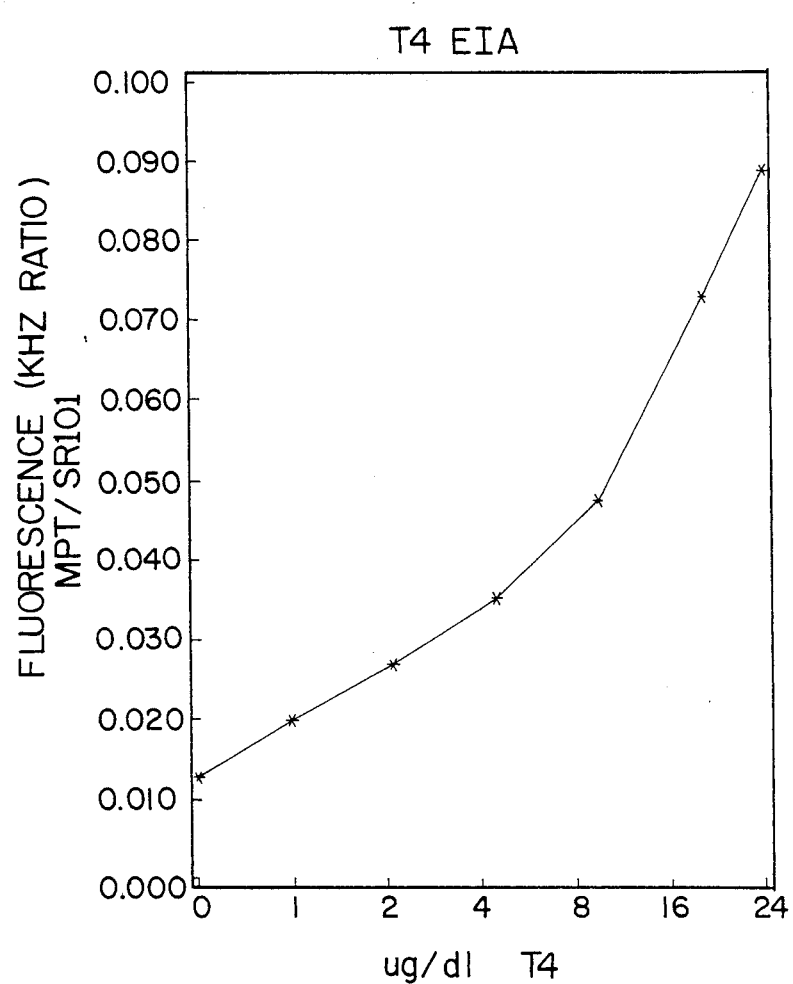
FIG. 7 is a graphic representation of a ratio of fluorescence signals measured as a function of the concentration of thyroxine ($T_4$), carrying out the principles of the present invention in an enzyme immunoassay of the competitive type.

A light transparent polystyrene tube had its interior surfaces coated with anti-T4. To the coated tube was added 300 microliters of a 1:15,000 dilution of peroxidase-labeled $T_4$ conjugate and 25 microliters of a sample to be tested for, and believed to contain, $T_4$. The reaction was allowed to proceed for 15 minutes at 37° C., and the incubate was then aspirated. The tube was washed six times with 0.5 milliliters each of 0.5% Tween-20 in water. To the washed tube was added 300 microliters of substrate containing TMB and hydrogen peroxide, and the two fluorophores MPT and SR 101. The reaction was allowed to proceed for 15 minutes at 37° C, and the reaction was stopped by the addition of 0.8 milliliters of 1M citric acid. The tube was then read in a fluorometer as described in Example III, and the ratio of MPT/SR 101 was plotted as a function of the amount of $T_4$ originally added to the tube. Typical data is illustrated in FIG. 7.

Thus, the present invention relies on the ratio of light signals for the indirect colorimetric detection of an analyte of interest. Use of the ratio technique as described herein provides an internal correction mechanism which negates differences in length of light path, optical quality of the tube, tube positioning, variations in lamp output and similar factors which affect the optics of the system. In conventional colorimetry, differences such as fluctuation in lamp output and path length are typically corrected by using a double beam spectrometer and matched cuvettes for all measurements. Since the detector used in the present invention does not employ a double beam and a different cuvette is used for each measurement, the ratio techniques described herein serve as an effective way for minimizing these effects.

What is claimed is:

1. A method employing an enzyme immunoassay for measuring the concentration of an analyte in a sample by indirect colorimetric detection comprising:
   (a) combining a peroxidase-labeled antibody conjugate, a sample to be tested for an analyte, and an antibody bound to the interior surfaces of a transparent plastic tube so that the analyte binds to said bound antibody and said conjugate to form an immunologic complex in solid phase;
   (b) admixing into said tube a liquid solution containing a tetramethylbenzidine and hydrogen peroxide to cause a reaction with said immunologic complex and to activate the tetramethylbenzidine for a colorimetric response;
   (c) adding to said admixture a particle-containing solution which terminates said reaction and causes a stable particulate suspension to result;
   (d) directing incident light at a plurality of wavelengths through said tube into said suspension, a first wavelength of said incident light being substantially at 450nm at which activated tetramethylbenzidine attenuates by absorption the amount of light scattered from said incident light as a function of the increasing concentration of the analyte present, a second wavelength being spectrally removed from said first wavelength and at which substantially no attenuation of light scatter occurs as the concentration of the analyte increases;
   (e) detecting light scattered by the suspension at said first and at said second wavelengths and forming a ratio of said two respective wavelengths; and
   (f) comparing the magnitude of said formed ratio with the magnitude of a ratio associated with light scatter detection when steps (a) to (e) are performed with samples containing known concentrations of said analyte, whereby the concentration of the analyte in the sample is measured.

2. The method of claim 1 wherein the analyte is selected from the group consisting of human chorionic gonadotropin and luteinizing hormone.

3. A method employing an enzyme immunoassay for measuring the concentration of an analyte in a sample by indirect colorimetric detection comprising:
   (a) combining a peroxidase-labeled antibody conjugate, a sample to be tested for an analyte, and an antibody bound to the interior surfaces of a transparent plastic tube so that the analyte binds to said bound antibody and said conjugate to form an immunologic complex in solid phase;
   (b) admixing into said tube a liquid solution containing a tetramethylbenzidine and hydrogen peroxide to cause a reaction with said immunologic complex and to activate the tetramethylbenzidine for a colorimetric response;
   (c) adding to said admixture a first fluorphore for causing fluorescence at or near the absorbance maxima of activated tetramethylbenzidine as a function of the increasing concentration of the analyte present in the sample;
   (d) adding to said admixture a second fluorophore which has substantially no attenuation of its fluorescence as the concentration of the analyte increases;
   (e) directing incident light at a plurality of wavelengths through said tube into said last-mentioned admixture, said wavelengths including a wavelength at or near said absorbance maxima of activated tetramethylbenzidine, and including wavelengths for causing excitation of said first and said second fluorophores;
   (f) detecting fluorescence emitted by the fluorophores and forming a ratio of the two fluorescence wavelengths; and (g) comparing the magnitude of said formed ratio with the magnitude of a ratio associated with fluorescence detection when steps (a) to (f) are performed with samples containing known concentrations of said analyte, whereby the concentration of the analyte in the sample is measured.

4. A method employing an enzyme immunoassay for measuring the concentration of an analyte in a sample by indirect colorimetric detection comprising:

(a) combining a peroxidase-labeled analyte conjugate, a sample to be tested for an analyte, and an antibody bound to the interior surfaces of a transparent plastic tube so that the analyte competes with the enzyme labeled analyte conjugate for binding with said bound antibody to form a solid phase;

(b) admixing into said tube a liquid solution containing a tetramethylbenzidine and hydrogen peroxide to cause a reaction with said bound enzyme and to activate the tetramethylbenzidine for a colorimetric response;

(c) adding to said admixture a particle-containing solution which terminates said reaction and causes a stable particulate suspension to result;

(d) directing incident light at a plurality of wavelengths through said tube into said suspension, a first wavelength of said incident light being substantially at 450 nm at which activated tetramethylbenzidine absorbs an amount of light available for scatter from said incident light as a function of the increasing concentration of the analyte present, a second wavelength being spectrally removed from said first wavelength and at which substantially no attenuation of light scatter occurs as the concentration of the analyte increases;

(e) detecting light scattered by the suspension at said first and at said second wavelengths and forming a ratio of said two respective wavelengths; and (f) comparing the magnitude of said formed ratio with the magnitude of a ratio associated with light scatter detection when steps (a) to (e) are performed with samples containing known concentrations of said analyte, whereby the concentration of the analyte in the sample is measured.

* * * * *